US012303327B2

(12) United States Patent
Stigall et al.

(10) Patent No.: US 12,303,327 B2
(45) Date of Patent: May 20, 2025

(54) FLEXIBLE SUPPORT MEMBER FOR INTRALUMINAL IMAGING DEVICE AND ASSOCIATED DEVICES, SYSTEMS, AND METHODS

(71) Applicant: KONINKLIJKE PHILIPS N.V., Eindhoven (NL)

(72) Inventors: Jeremy Stigall, Carlsbad, CA (US); Jun Song, San Diego, CA (US)

(73) Assignee: PHLIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 16/967,531

(22) PCT Filed: Jan. 31, 2019

(86) PCT No.: PCT/EP2019/052308
§ 371 (c)(1),
(2) Date: Aug. 5, 2020

(87) PCT Pub. No.: WO2019/154699
PCT Pub. Date: Aug. 15, 2019

(65) Prior Publication Data
US 2021/0113180 A1    Apr. 22, 2021

Related U.S. Application Data

(60) Provisional application No. 62/628,340, filed on Feb. 9, 2018.

(51) Int. Cl.
*A61B 8/12*    (2006.01)
*A61B 8/00*    (2006.01)
(Continued)

(52) U.S. Cl.
CPC ............... *A61B 8/12* (2013.01); *A61B 8/445* (2013.01); *G01S 7/52079* (2013.01); *G01S 15/8915* (2013.01)

(58) Field of Classification Search
None
See application file for complete search history.

(56) References Cited

U.S. PATENT DOCUMENTS 6,641,540 B2    11/2003    Fleischman
6,776,763 B2    8/2004    Nix
(Continued)

FOREIGN PATENT DOCUMENTS

WO    2017167883 A1    10/2017
WO    2017168290 A1    10/2017
(Continued)

OTHER PUBLICATIONS

International Search Report & Written Opinion of PCT/EP2019/052308, dated Apr. 10, 2019.

*Primary Examiner* — Shahdeep Mohammed

(57) ABSTRACT

Intraluminal ultrasound imaging devices, methods, and systems are provided. Some embodiments of the present disclosure include intraluminal devices configured to navigate and maneuver tortuous vasculature of a patient. For example, an intravascular imaging device can include a flexible support member at a distal portion of the imaging device. The flexible support member may support a plurality of ultrasound transducers and a plurality of control circuits. The flexible support member includes a flexible joint portion between a transducer portion and a controller portion. Introducing a flexible joint portion between the transducer portion and the controller portion can provide for greater flexibility of the imaging device and enable the device to navigate tortuous regions of a patients anatomy.

21 Claims, 12 Drawing Sheets

(51) Int. Cl.
*G01S 7/52* (2006.01)
*G01S 15/89* (2006.01)

(56) References Cited

U.S. PATENT DOCUMENTS

| | | | | |
|---|---|---|---|---|
| 7,226,417 | B1* | 6/2007 | Eberle | B06B 1/0633 |
| | | | | 29/25.35 |
| 7,846,101 | B2 | 12/2010 | Eberle | |
| 8,052,706 | B2* | 11/2011 | Mitusina | A61B 17/32002 |
| | | | | 606/180 |
| 2004/0044286 | A1* | 3/2004 | Hossack | A61B 8/445 |
| | | | | 600/585 |
| 2004/0193057 | A1* | 9/2004 | Barbato | A61B 5/06 |
| | | | | 600/459 |
| 2007/0156048 | A1 | 7/2007 | Panescu | |
| 2008/0089180 | A1* | 4/2008 | Matsumoto | B06B 1/0292 |
| | | | | 367/181 |
| 2008/0089181 | A1* | 4/2008 | Adachi | A61B 8/12 |
| | | | | 367/189 |
| 2008/0200811 | A1* | 8/2008 | Wakabayashi | B06B 1/0292 |
| | | | | 73/632 |
| 2008/0294158 | A1* | 11/2008 | Pappone | A61B 18/1492 |
| | | | | 606/41 |
| 2010/0010526 | A1* | 1/2010 | Mitusina | A61B 17/32002 |
| | | | | 606/171 |
| 2010/0030217 | A1* | 2/2010 | Mitusina | A61B 17/32002 |
| | | | | 606/180 |
| 2010/0145310 | A1* | 6/2010 | Lee | A61M 25/0105 |
| | | | | 604/528 |
| 2011/0022069 | A1* | 1/2011 | Mitusina | A61B 17/32002 |
| | | | | 606/180 |
| 2011/0130648 | A1* | 6/2011 | Beeckler | A61B 18/1492 |
| | | | | 600/424 |
| 2012/0095347 | A1* | 4/2012 | Adam | G01S 7/52079 |
| | | | | 600/459 |
| 2013/0303919 | A1 | 11/2013 | Corl | |
| 2014/0088630 | A1 | 3/2014 | Tran | |
| 2015/0305710 | A1 | 10/2015 | Stigall | |

FOREIGN PATENT DOCUMENTS

| | | |
|---|---|---|
| WO | 2018060369 A1 | 4/2018 |
| WO | 2018141949 A1 | 8/2018 |

* cited by examiner

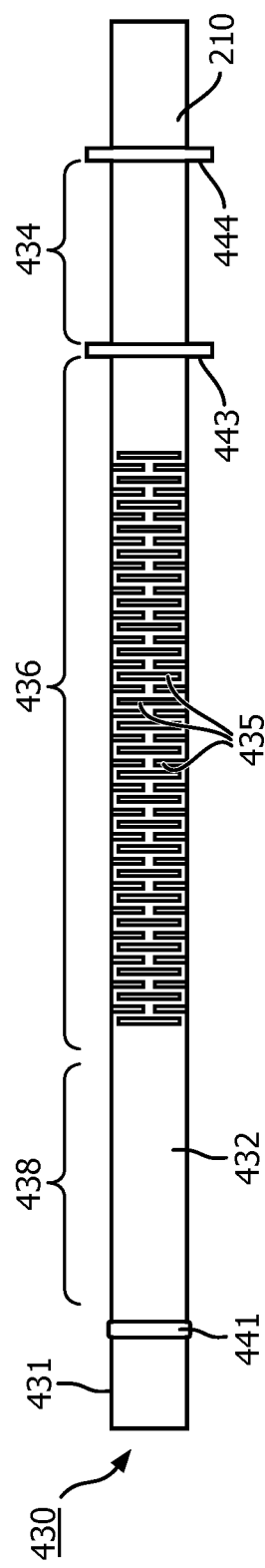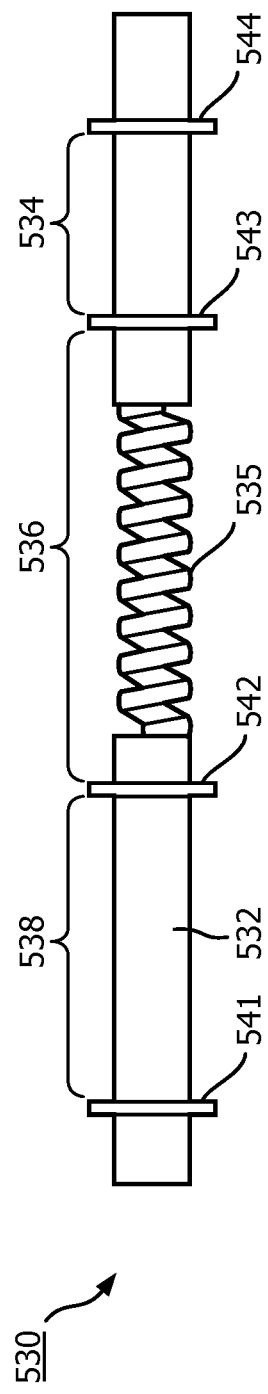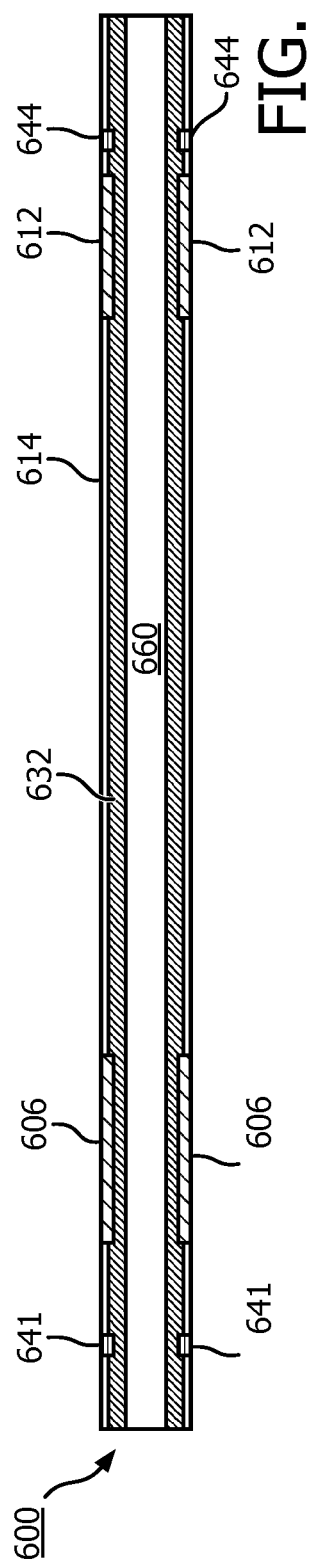

FLEXIBLE SUPPORT MEMBER FOR INTRALUMINAL IMAGING DEVICE AND ASSOCIATED DEVICES, SYSTEMS, AND METHODS

RELATED APPLICATION

This application claims the benefit of and priority to U.S. Provisional No. 62/628,340, filed Feb. 9, 2018, which is incorporated by reference herein.

TECHNICAL FIELD

The present disclosure relates generally to intraluminal imaging, such as intravascular ultrasound (IVUS) imaging, and, in particular, to the distal structure of an intraluminal imaging device. For example, the distal structure can include a support member and a flex circuit that are arranged to facilitate efficient assembly and operation of the intraluminal imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in the form of ultrasonic waves in order to create an image of the vessel of interest. The ultrasonic waves are partially reflected by discontinuities arising from tissue structures (such as the various layers of the vessel wall), red blood cells, and other features of interest. The reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse physiology within the human body is challenging. In that regard, components at the distal portion of the imaging device cause an area of high rigidity in the intravascular device, which increases the likelihood of kinking as the intravascular device is steered through tortuous vasculature. In some instances, the area of high rigidity can limit the ability of the imaging device to navigate and maneuver through particularly tortuous regions of the vasculature.

SUMMARY

The present disclosure advantageously describes intravascular imaging devices configured to navigate and maneuver tortuous vasculature of a patient. For example, an intravascular imaging device can include a flexible support member at a distal portion of the imaging device. The flexible support member includes a flexible joint portion between a transducer portion and a controller portion. Introducing a flexible joint portion between the transducer portion and the controller portion can provide for greater flexibility of the imaging device and enable the device to navigate tortuous regions of a patient's anatomy.

In some aspects, an intraluminal ultrasound imaging device includes a plurality of ultrasound transducer elements configured to obtain imaging data, a plurality of control circuits in communication with the plurality of ultrasound transducer elements, a plurality of conductive traces extending between the plurality of ultrasound transducer elements and the plurality of control circuits, a flexible elongate body configured to be positioned within a body lumen of a patient, and a support member coupled to a distal portion of the flexible elongate body. The support member can include a transducer portion adjacent to the plurality of ultrasound transducer elements, a control portion adjacent to the plurality of control circuits, and a flex joint portion comprising a flexible element disposed between the transducer portion and the control portion. The flex joint portion is adjacent to the plurality of conductive traces, and the joint portion is more flexible than the transducer portion and the control portion, in some embodiments.

In some embodiments, the support member is generally cylindrical. The support member may comprise stainless steel. In some embodiments, the support member can include a polymer and a conductive agent. The flex joint portion can include a plurality of cuts. In other embodiments, the polymer may include an acoustic dampening material. In still other embodiments, the flex joint portion comprises a coil coupled to the transducer portion and the control portion. The flexible substrate may be positioned around the support member, in some aspects, and the plurality of conductive traces may be coupled to the flexible substrate. The support member can include an elongate body and one or more flanges coupled to the elongate body, wherein an outer diameter of the one or more flanges is greater than an outer diameter of the elongate body. The device may further include an acoustic backing material disposed between the elongate body and the plurality of ultrasound transducer elements. The flexible substrate can include one or more slot openings configured to facilitate flexing of the flexible substrate. The flexible substrate can also comprise one or more grounding regions in communication with the support member.

According to some embodiments, the plurality of ultrasound transducer elements comprises an ultrasonic transducer array disposed in an annular configuration around the transducer portion of the support member. In other embodiments, the device includes a shrink tubing positioned around and configured to hermetically seal at least one of: the plurality of ultrasound transducer elements; the plurality of control circuits; or the plurality of communication lines. The support member can further include a first flange at a proximal portion of the transducer portion and a second flange at a distal portion of the transducer portion, wherein the first flange and second flange are configured to space the plurality of transducer elements from the support member. In some aspects, the support member includes a third flange at a proximal portion of the control portion and a fourth flange at a distal portion of the control portion. The third flange and fourth flange can be configured to support the plurality of control circuits.

According to other aspects of the present disclosure, an intraluminal ultrasound imaging system is provided that includes an intraluminal imaging device and a computing device. The intraluminal imaging device includes a flexible elongate body configured to be positioned within a body lumen of a patient, and an imaging assembly disposed at a distal portion of the flexible elongate body and configured to obtain imaging data associated with the body lumen. The imaging assembly includes a support member around which a plurality of transducer elements, a plurality of control circuits, and a plurality of communication lines are positioned. The support member can include a transducer portion adjacent to the plurality of transducer elements, a control portion adjacent to the plurality of control circuits, and a flex joint portion. The flex joint portion can comprise a flexible element disposed between the transducer portion and the control portion. The flex joint portion can be adjacent to the plurality of communication lines, and can be more flexible than the transducer portion and the control portion. In some aspects, the computing device is in communication with the intraluminal imaging device and configured to output, to a display, an image of the body lumen based on the obtained imaging data.

In some embodiments, the intraluminal imaging device includes a catheter. In other embodiments, the intraluminal imaging device comprises an intravascular ultrasound (IVUS) device. Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 14 is a diagrammatic side view of a support member, according to aspects of the present disclosure.

FIG. 15 is a diagrammatic side view of a support member, according to aspects of the present disclosure.

FIG. 16 is a diagrammatic side view of a polymeric support member and a flex circuit in a rolled configuration, according to aspects of the present disclosure.

DETAILED DESCRIPTION

Figure 1:
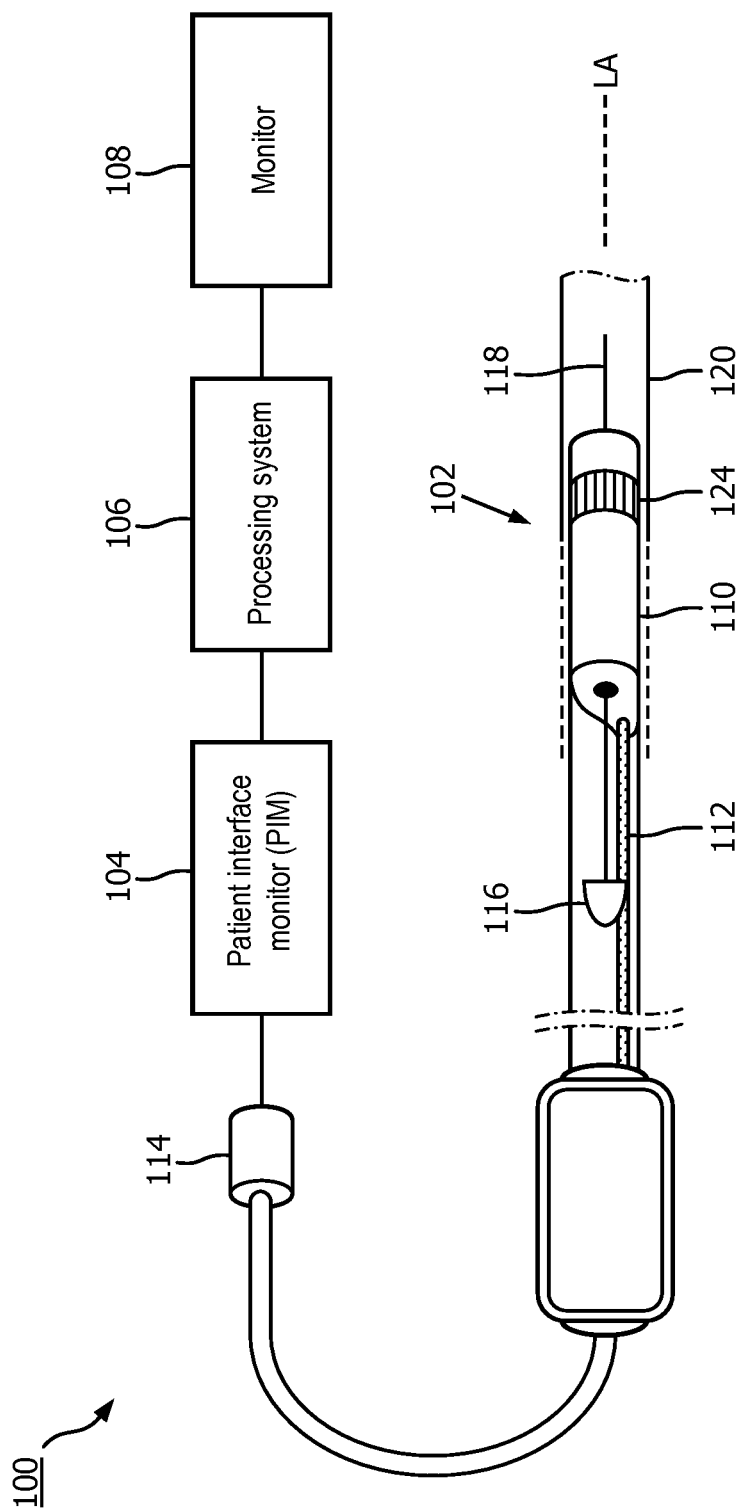
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. For example the system 100 can be an intravascular ultrasound (IVUS) imaging system. The imaging system 100 may include an intraluminal ultrasound imaging device 102 (such as a solid-state or phased array IVUS device), a patient interface module (PIM) 104, a processing system or console 106, and a monitor 108. The device 102 can be a catheter guide wire, or guide catheter.

At a high level, the IVUS device 102 emits ultrasonic energy from a transducer array 124 included in a scanner assembly 110 mounted near a distal end of the catheter device. For the purposes of this disclosure, the scanner assembly 110 may also be referred to as a flex circuit or an imaging assembly, in some instances. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on a non-transitory tangible computer readable medium.

The PIM 104 facilitates communication of signals between the IVUS console 106 and the scanner assembly 110 included in the IVUS device 102. This communication includes the steps of: (1) providing commands to control logic dies 206A, 206B, illustrated in FIG. 2, included in the scanner assembly 110 to select the particular transducer array element(s) to be used for transmit and receive, (2) providing the transmit trigger signals to the control logic dies 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the control logic die(s) 206 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be referenced as a body lumen of the patient. The body lumen or vessel 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, Dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
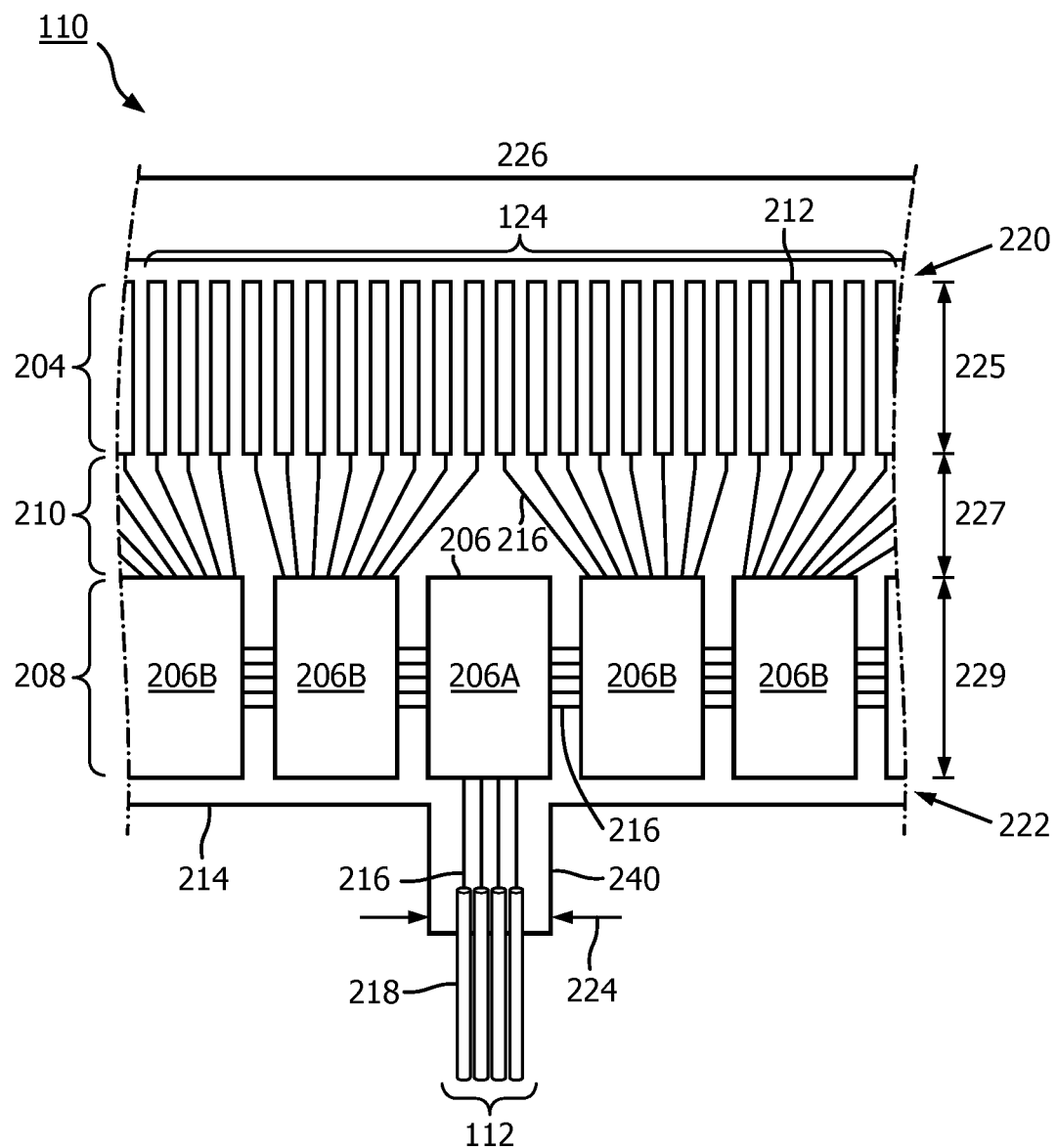
FIG. 2 is a diagrammatic top view of a flex circuit in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

Figure 3:
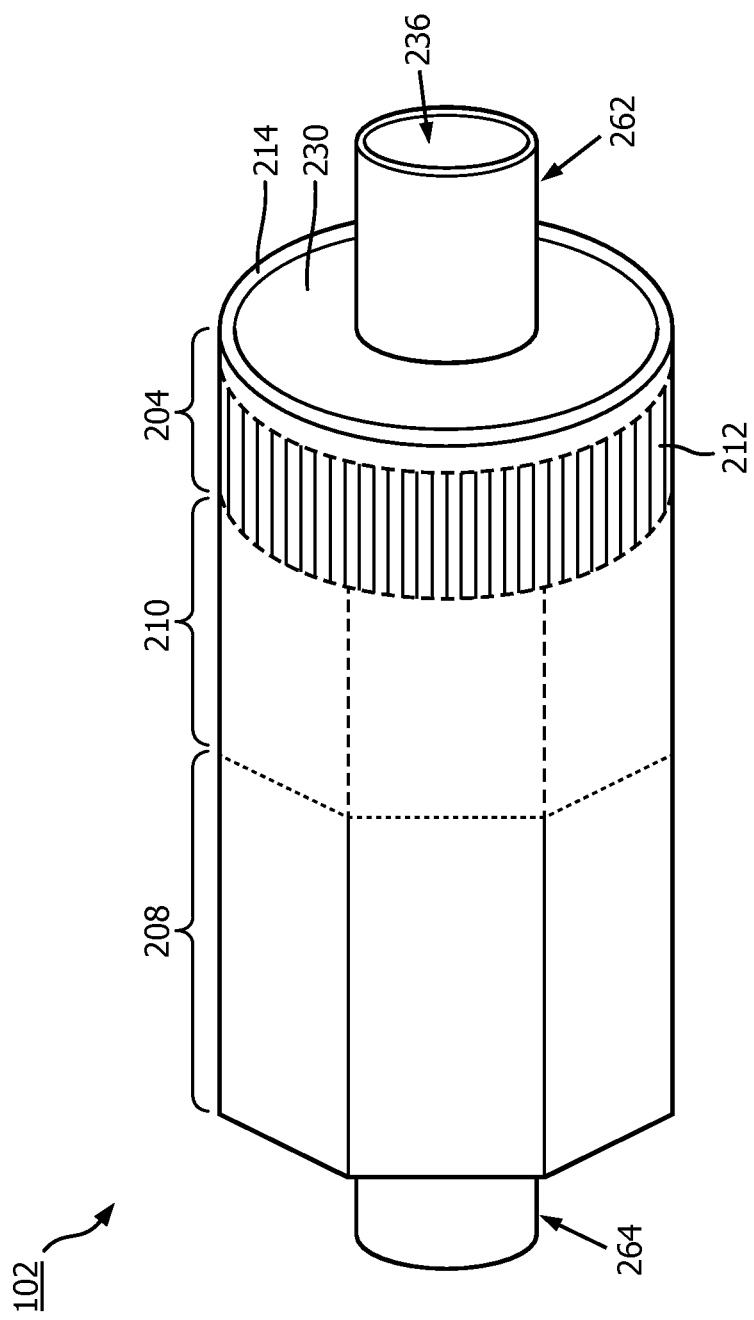
FIG. 3 is a diagrammatic side view of a flex circuit in a rolled configuration around a support member, according to aspects of the present disclosure.

FIG. 2 is a top view of a portion of an ultrasound scanner assembly, or flex circuit 214, according to an embodiment of the present disclosure. The flex circuit 214 includes a transducer array 124 formed in a transducer region 204 and transducer control logic dies 206 (including dies 206A and 206B) formed in a control region 208, with a transition region 210 disposed therebetween. For the purposes of this disclosure, the transducer control logic dies 206 may also be referred to as control circuits. The transducer control logic dies 206 and the transducers 212 are mounted on a flexible substrate or film whereon various electrical components can be formed and/or attached. FIG. 3 illustrates a rolled configuration of the flex circuit 214. The transducer array 124 is a non-limiting example of a medical sensor element and/or a medical sensor element array. The transducer region 204 is disposed adjacent a distal portion 220 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the embodiments of FIGS. 2 and 3 are described as including a flex circuit, it is understood that the transducers and/or controllers may be arranged in other configurations, including those omitting a flex circuit.

The transducer array 124 may include any number and type of ultrasound transducers 212, or ultrasound transducer elements, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The flex circuit 214 may include various transducer control logic, which in the illustrated embodiment is divided into discrete control logic dies 206. In various examples, the control logic of the flex circuit 214 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, the flex circuit 214, having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled flex circuit 214. In some embodiments, the film layer is between 5 µm and 100 µm, with some particular embodiments being between 12.7 µm and 25.1 µm.

To electrically interconnect the control logic dies 206 and the transducers 212, in an embodiment, the flex circuit 214 further includes conductive traces 216 formed on the film layer that carry signals between the control logic dies 206 and the transducers 212. In some instances, the conductive traces 216 can be referred to as communication lines. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flex circuit 214 may be further determined by the width of the conductor 218 to be coupled to the trace/pad.

The flex circuit 214 can include a conductor interface 240, or interface region, in some embodiments. The conductor interface 240 can be a location of the flex circuit 214 where the conductors 218 of the cable 114 are coupled to the flex circuit 214. For example, the bare conductors of the cable 114 are electrically coupled to the flex circuit 214 at the conductor interface 240. The conductor interface 240 can be a tab extending from the main body of flex circuit 214. In that regard, the main body of the flex circuit 214 can refer collectively to the transducer region 204, controller region 208, and the transition region 210. In the illustrated embodiment, the conductor interface 240 extends from the proximal portion 222 of the flex circuit 214. In other embodiments, the conductor interface 240 is positioned at other parts of the flex circuit 214, such as the distal portion 220, or the flex circuit 214 omits the conductor interface 240. A value of a dimension of the tab or conductor interface 240, such as a width 224, can be less than the value of a dimension of the main body of the flex circuit 214, such as a width 226. In some embodiments, the substrate forming the conductor interface 240 is made of the same material(s) and/or is similarly flexible as the flex circuit 214. In other embodiments, the conductor interface 240 is made of different materials and/or is comparatively more rigid than the flex circuit 214. For example, the conductor interface 240 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 240 and/or the conductor(s) 218 can be variously configured to facilitate efficient manufacturing and operation of the flex circuit 214.

Figure 4:
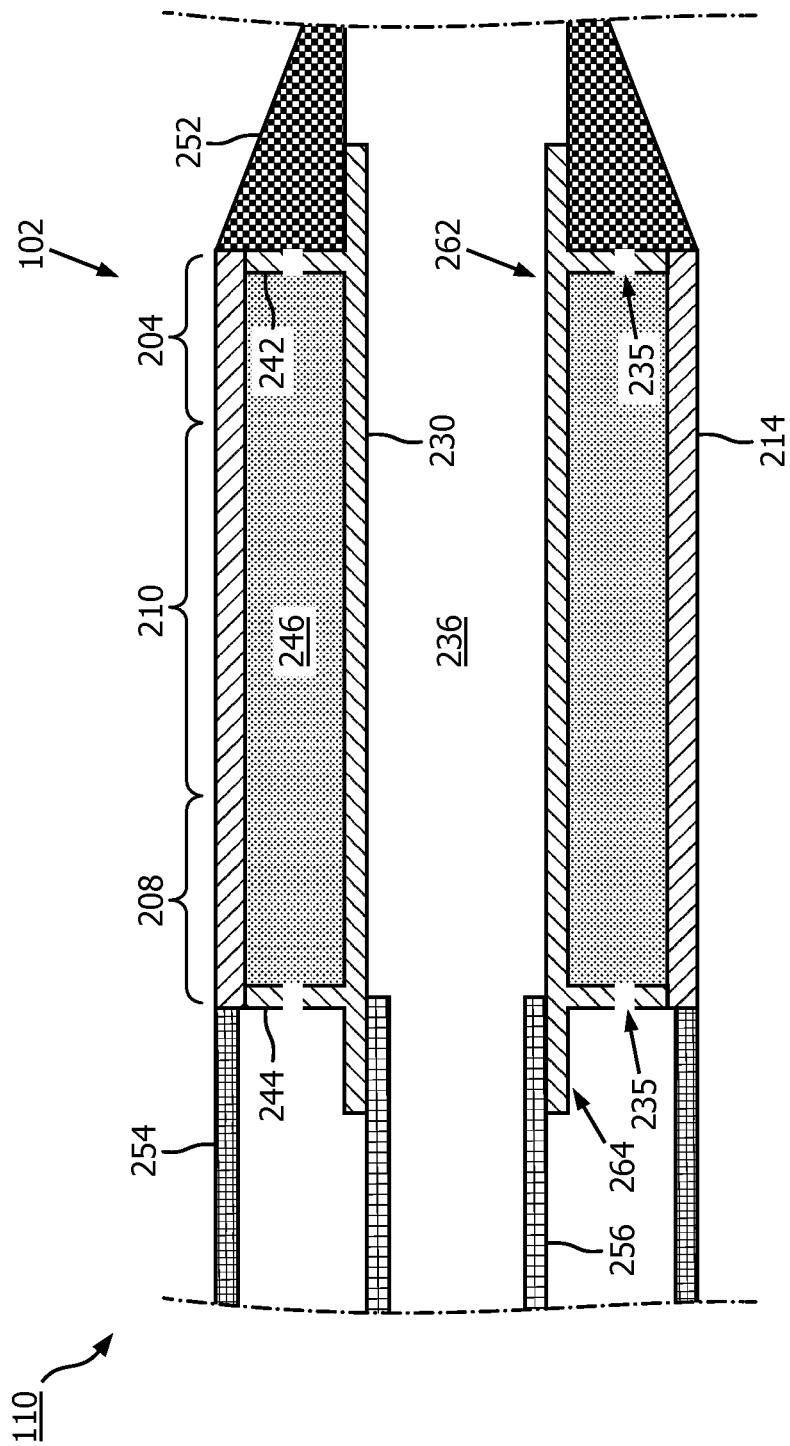
FIG. 4 is a diagrammatic cross-sectional side view of a distal portion of an intravascular device, according to aspects of the present disclosure.

In some instances, the flex circuit 214 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRA- SOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view of an intravascular imaging device 102 with the flex circuit 214 in a rolled configuration around a support member 230, according to aspects of the present disclosure. FIG. 4 is a diagrammatic cross-sectional side view of a distal portion of the intravascular device 102, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and flanges 242, 244, that are fixedly coupled to one another.

Flanges 242, 244 that extend outward from the support member 230 are provided at the distal and proximal portions 262, 264, respectively, of the support member 230. The flanges 242, 244 support the distal and proximal portions of the flex circuit 214. In that regard, portions of the flex circuit 214, such as the transducer region 204, can be spaced from a central body portion of the support member 230 extending between the flanges 242, 244. The flanges 242, 244 can have the same outer diameter or different outer diameters. For example, the distal flange 242 can have a larger or smaller outer diameter than the proximal flange 244. To improve acoustic performance, a cavity between the flex circuit 214 and the surface of the support member 230 can be filled with a backing material 246. The backing material 246 can be introduced between the flex circuit 214 and the support member 230 via passageways 235 in the flanges 242, 244. In some embodiments, suction can be applied via the passageways 235 of one of the flanges 242, 244, while the backing material 246 is fed between the flex circuit 214 and the support member 230 via the passageways 235 of the other of the flanges 242, 244. In some embodiments, the backing material can be a liquid. The backing material can be cured to allow it to solidify and set. In various embodiments, the support member 230 includes more than two flanges 242, 244, only one of the flanges 242, 244, or neither of the flanges. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inside diameter of the support member 230 (e.g., the diameter of the lumen 236) can correspondingly increase or decrease as the outer diameter changes. In other embodiments, the inside diameter of the support member 230 remains the same despite variations in the outer diameter. In other embodiments, the inside diameter of the support member 230 can change while the outer diameter remains the same.

In some embodiments, the transducer elements 212, array 124, and/or the controllers 206 can be positioned in an annular configuration, such as a circular configuration or in a polygon configuration, around a longitudinal axis LA of the imaging device 102 (FIG. 1). For example, a cross-sectional profile of the imaging assembly 110 at the transducer elements 212, array 124, and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. The cross-section shape of the imaging device 102 in the regions 208, 210, 204 may be different. For example, the cross-sectional shape of the region 208 can be a nonagon, the cross-sectional shape of the region 210 can be approximately circular, and the cross-sectional shape of the region 204 can be polygonal (with the number of sides of the polygon equaling the number of transducer elements 212 in the array 124).

A proximal inner member 256 and a proximal outer member 254 are coupled to the proximal portion 264 of the support member 230. The proximal inner member 256 and/or the proximal outer member 254 can be a flexible elongate body that extends from proximal portion of the intravascular device 102, such as the proximal connector 114, to the flex circuit 214. For example, the proximal inner member 256 can be received within the proximal portion 264. The proximal outer member 254 abuts and is in contact with the flex circuit 214. A distal member 252 is coupled to the distal portion 262 of the support member 230. The distal member 252 can be a flexible component that defines a distal most portion of the intravascular device 102. For example, the distal member 252 is positioned around the distal portion 262. The distal member 252 can abut and be in contact with the flex circuit 214 and the flange 242. The distal member 252 can be the distal-most component of the intravascular device 102.

One or more adhesives can be disposed between various components at the distal portion of the intravascular device 102. For example, one or more of the flex circuit 214, the support member 230, the distal member 252, the proximal inner member 256, and/or the proximal outer member 254 can be coupled to one another via an adhesive.

Figure 5:
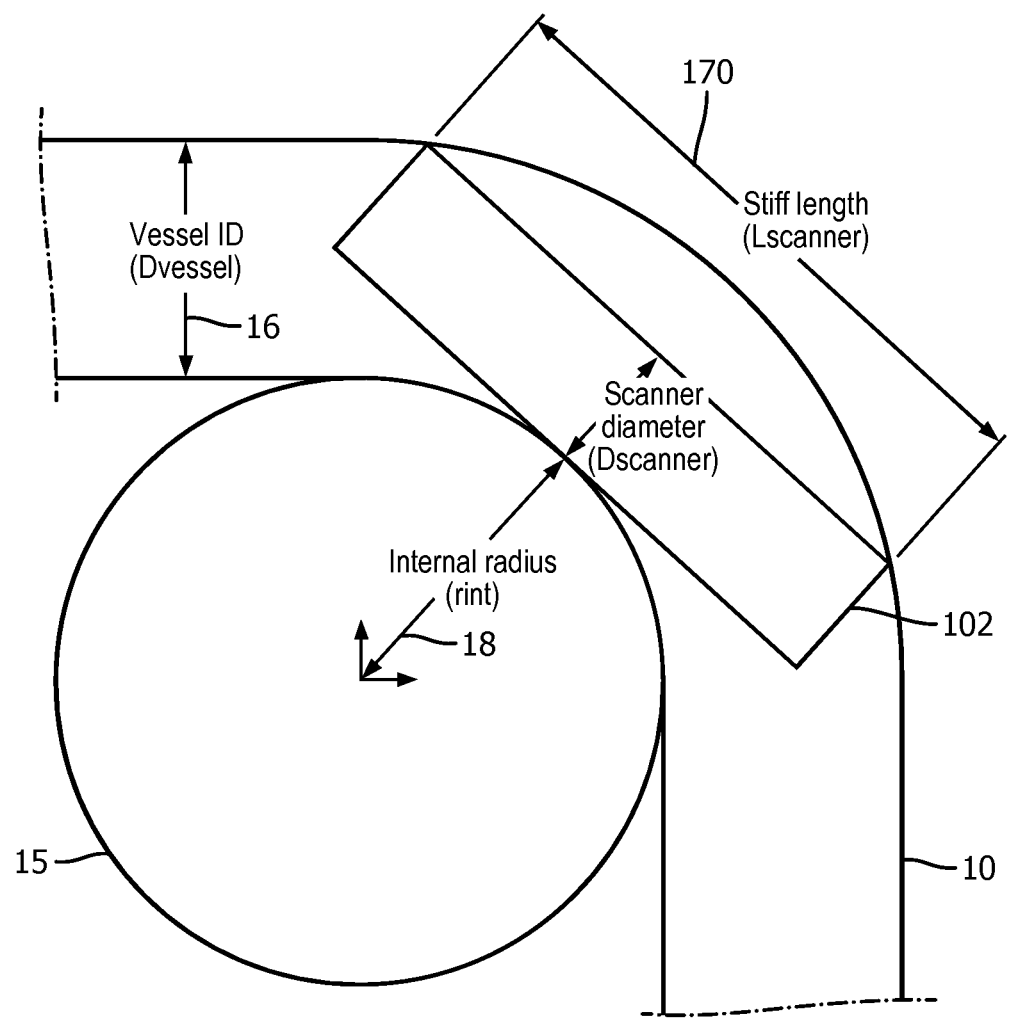
FIG. 5 is a diagrammatic top view of an intravascular device in a tortuous portion of a blood vessel, according to aspects of the present disclosure.

FIG. 5 illustrates an embodiment of a distal portion of an intravascular imaging device 102 inside a vessel 10 of a patient. The vessel 10 comprises a bend that can be partially characterized by an inside diameter 16, and a circle 15 having a radius 18. In that regard the bend of the blood vessel 10 can be described as following a portion of the circumference of the circle 15. The imaging device 102 can comprise a plurality of the components described above with respect to FIGS. 3 and 4, including a support member and a flex circuit. In some embodiments, the imaging device 102 has a so-called "stiff length" 70 partially characterized by the geometry of the support member and the flex circuit. The stiff length 70 may determine the types of vasculature through which the imaging device 102 can traverse.

For example, in embodiments comprising a rigid support member having a length L, the stiff length 70 of the distal portion of the imaging device 102 may be the length L. The stiff length 70 may also be characterized, in part, by a width of the distal portion of the imaging device 102. As the distal portion of the imaging device 102 navigates to the bend in the blood vessel 10, the shape, size, and configuration of the distal portion of the imaging device 102, including the stiff length 70, can limit the regions of the patient's vasculature through which the imaging device 102 can travel. The bend in the vessel 10 of FIG. 5 may be the most tortuous path through which the imaging device 102 can traverse. In other words, the imaging device 102 of FIG. 5 may not be able to pass through vessels having a sharper bend than the vessel 10 of FIG. 5 and/or vessels having an inside diameter smaller than the inside diameter 16 of the vessel 10 of FIG. 5. Attempting to force an imaging device having a relatively large stiff length through tortuous vasculature could result in damage to the vessel 10 tissue or structure.

Figure 6:
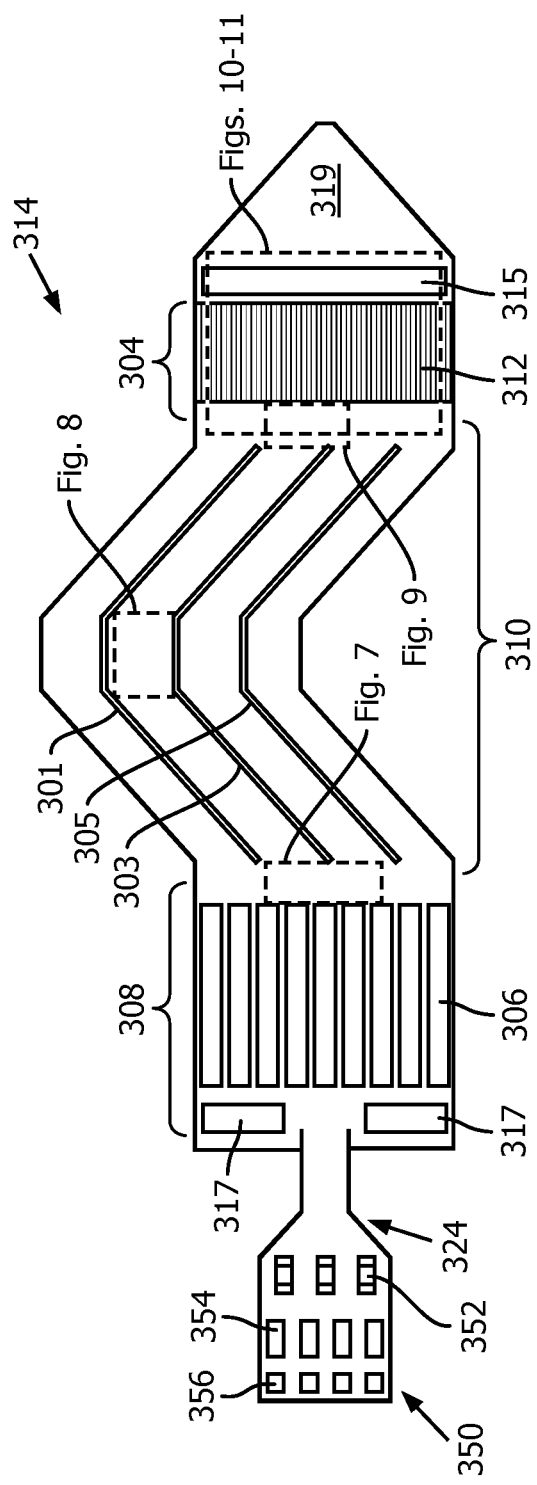
FIG. 6 is a diagrammatic top view of a flex circuit in a flat configuration, according to aspects of the present disclosure.

FIG. 6 illustrates exemplary embodiment of a flex circuit 314 or flexible substrate in a flat configuration. At least a portion of the flex circuit 314, such as a transition region 310 can be shaped and configured to improve flexibility of the intravascular device. As described below with respect to FIG. 13, a support member 330 around which the flex circuit 314 is positioned can be shaped to compliment the orientation of the flex circuit 314 around the support member 330. The flex circuit 314 and the support member 330 can be shaped to advantageously increase the flexibility of intravascular device and decrease the likelihood of kinking while the intravascular device is navigated through a patient's vasculature. The flex circuit 314 can be positioned at a distal portion of an intravascular device (e.g., device 102).

The flex circuit 314 can be similar in some respects to the flex circuit 214 of FIG. 2. The flex circuit 314 includes a transducer region 304 having a plurality of transducers 312 at a distal portion 320 and a controller region 308 having plurality of control circuits 306 at a proximal portion 322. A transition region 310 having a plurality of conductive traces 316 extending between the controller and transducer regions 308, 304 facilitates communication between the plurality of transducers 312 and the plurality of control circuits 306. The flex circuit 314 can comprise a flexible substrate on which the conductive traces 316 are formed. Similar to the flex circuit 214 of FIG. 2, the transition region 310 can have a width of any suitable value, including between approximately 0.2 mm and 10 mm. The transducer region 304 and/or the controller region 308 can have widths between approximately 1 mm" and 10 mm, for example. Another dimension of the flex circuit 314, such as a length, can have a larger value than a corresponding dimension, such as lengths of the transducer region 304 and the controller region 308, respectively. The length of the transition region can be any suitable value, including between approximately 0.1 mm and 12 mm. The length of the transducer region 304 can be between approximately 0.5 mm and 6 mm for example. The length of the controller region 308 can be between approximately 0.5 mm and 8 mm for example.

The flex circuit 314 can comprise a flexible substrate or film. The transition region 310 of the flex circuit 314 can comprise one or more relief cuts 301, 303, 305, slots, or openings, configured to provide enhanced flexibility of the flex circuit 314 to be wrapped, rolled, or otherwise disposed around a support member. The relief cuts 301, 303, 305 extend longitudinally along the length of the flexible substrate 314 within the transition region 310. The cuts 301, 303, 305 may extend parallel to one another. Referring to the embodiment of FIG. 6, the flex circuit 314 comprises three relief cuts 301, 303, 305 configured to increase flexibility of the flex circuit 314. In some embodiments, the flex circuit 314 can include more or fewer relief cuts than the embodiment illustrated in FIG. 6. For example, the flexible substrate 314 can include zero, one, two, three, four, five, six, or more cuts. In some embodiments, the flex circuit 314 comprises no relief cuts. In some embodiments, the flex circuit 314 can comprise other means of enhancing flexibility, such as one or more perforations, creases, and/or areas of decreased thickness of the flexible substrate.

The transition region 310 is depicted in a trapezoidal fashion for illustrative purposes only, and does not necessarily depict the layout of the flex circuit 314. For example, the transition region 310 may be rectangular, and the relief cuts 301, 303, 305, may comprise linear cuts. In other embodiments, the transition region 310 may comprise a parallelogram shape, a concave shape, or any other suitable shape.

The flex circuit 314 includes grounding regions 315, 317, including a distal grounding region 315 and a proximal grounding region 317. The distal grounding region 315 can be disposed near a distal end 319 of the flex circuit 314, distal of the plurality of transducers 312. In other embodiments, the distal grounding region 315 can be disposed proximal to the transducers 312. The proximal grounding region 317 can be disposed near a proximal portion 324 of the flex circuit 314. As further explained below, the grounding regions 315, 317 can be configured to abut or contact one or more conductive regions, such as flanges, of a support member to facilitate grounding of one or more components of the flex circuit 314 (e.g., transducers 312 and controllers 306). In some embodiments, the flex circuit 314 can include more or fewer grounding regions than the embodiment illustrated in FIG. 6. For example, in some embodiments, a flex circuit 314 can include a single grounding region configured to facilitate electrical grounding for the flex circuit 314. In other embodiments, the flex circuit 314 may have no grounding regions. In yet other embodiments, the flex circuit 314 can include 3, 4, or more grounding regions.

The flex circuit 314 comprises an interface region 350 at a proximal portion 324 of the flex circuit. The interface region 350 comprises a plurality of components configured to interface and/or couple to other components of an intravascular imaging device and/or imaging system. Interface region 350 comprises a plurality of capacitors 352 which can be configured to modify imaging data received by the plurality of transducers 312. In some embodiments, the capacitors 352 can be configured to reduce noise included in the imaging data obtained by the plurality of transducers 312. Interface region 350 also includes a plurality of connector regions 354 and testing regions 356. The connector regions 354 can comprise conductive regions or pads configured to provide an electrical connection between the flex circuit 314 and other components of an imaging device and/or imaging system. For example, in some embodiments, the connector regions 354 comprise a plurality of soldering pads. Testing regions 356 can be configured similarly to the connector regions 354, in some aspects. In some embodiments, the testing regions 356 may be in communication with the connector regions 354. The testing regions 356 can be configured to provide a communication interface with the components of the flex circuit 314 during manufacturing, assembly, and/or testing of the flex circuit. The testing regions 356 can be removed from the interface region 350 during or after assembly, in some cases. Although disposed at the proximal portion 324 of the flex circuit 314, the interface region 350 can be disposed at other regions of the flex circuit, such as near the distal end 319, or near the transition region 310.

Figure 9:
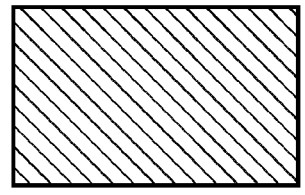
FIG. 9 is a diagrammatic top view of a conductive trace region of a flex circuit, according to aspects of the present disclosure.
Figure 8:
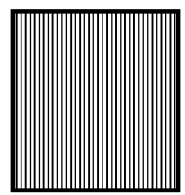
FIG. 8 is a diagrammatic top view of a conductive trace region of a flex circuit, according to aspects of the present disclosure.
Figure 7:
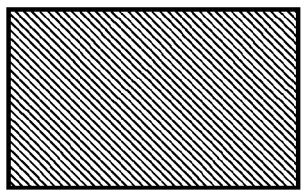
FIG. 7 is a diagrammatic top view of a conductive trace region of a flex circuit, according to aspects of the present disclosure.

FIGS. 7-9 respectively depict trace patterns of conductive traces of the controller region 308, the transition region 310, and the transducer region 304. Referring to FIG. 7, the conductive traces 316 of the controller region 308 may be arranged in an angled or slanted configuration with respect to an axis of the flex circuit 314. Referring to FIG. 8, the conductive traces 316 in the transition region 310 may be arranged in a linear or straight configuration with respect to an axis of the flex circuit 314. Referring to FIG. 9, the conductive traces 316 in the transducer region 304 may be arranged in a counter angle, or "zig-zag" configuration. Some of the patterns or arrangements shown in FIGS. 7-9 may increase the robustness of the flex circuit 314 in operation. For example, the angled configuration of FIG. 7 and the "zig-zag" configuration of FIG. 9 may protect the conductive traces 316 during frequent movements that apply strain, stress, and/or compression to the conductive traces 316 near the controller region 308 and/or the transducer region 304. The configurations of FIGS. 7 and 9 may allow for the flex circuit 314 to be rolled and installed on a support member, and to navigate tortuous regions of the patient's vasculature while mitigating a risk of kinking or fracturing one or more of the conductive traces 316.

This disclosure contemplates other configurations and patterns of conductive traces 316 than those shown in FIGS. 7-9. For example, in some embodiments, the conductive traces 316 at the transducer region 304 can have an angled configuration similar to that of FIG. 7. Moreover, in some embodiments, various regions of the flex circuit 314 can include conductive traces 316 in a zig-zag arrangement. In some embodiments, some or all of the regions of the flex circuit 314 can include an angled configuration similar to that of FIG. 7, and/or a straight configuration such as that of FIG. 8. Although not explicitly described, this disclosure contemplates other combinations of conductive trace patterns suitable to communicatively couple the plurality of transducers 312 to the plurality of control circuits 306.

Figure 10:
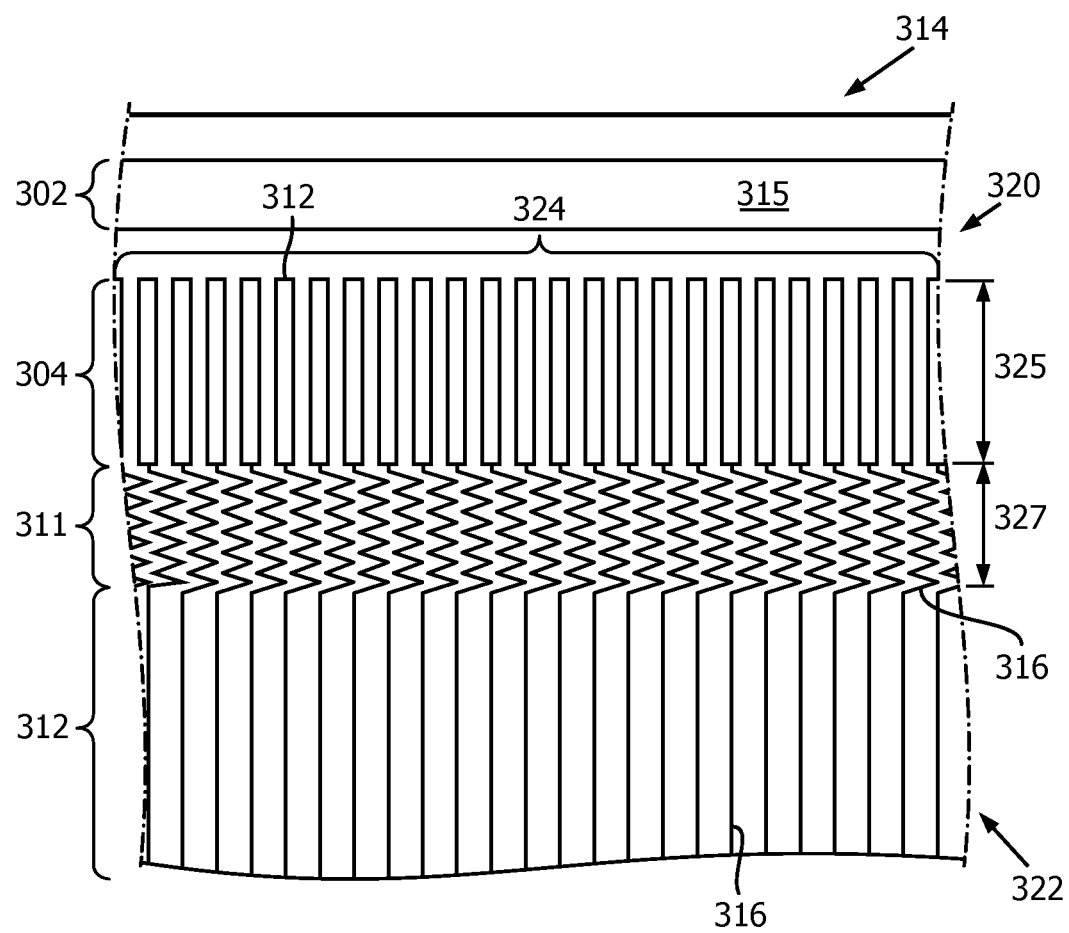
FIG. 10 is a diagrammatic top view of a portion of a flex circuit in a flat configuration, according to aspects of the present disclosure.
Figure 11:
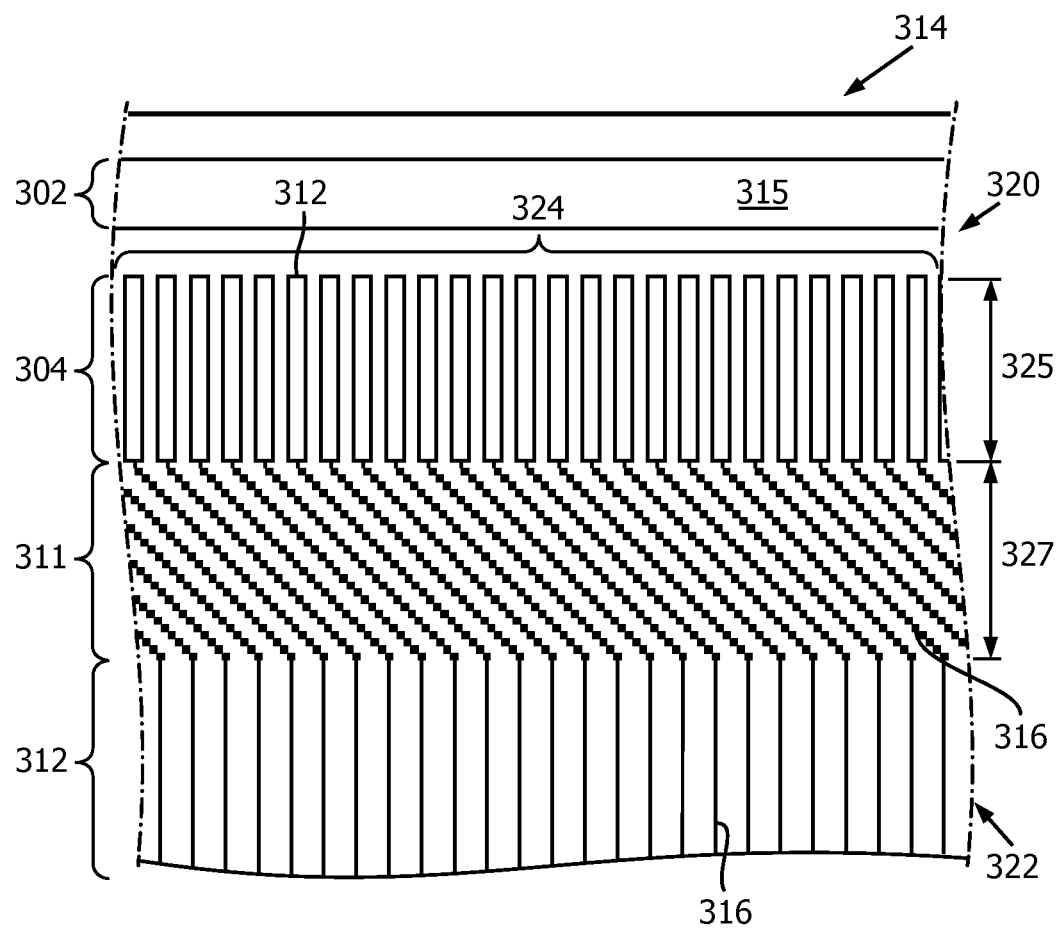
FIG. 11 is a diagrammatic top view of a portion of a flex circuit in a flat configuration, according to aspects of the present disclosure.

FIGS. 10 and 11 illustrate a distal portion of a flex circuit 314, including a transducer region 304, according to some embodiments. In particular, FIGS. 10 and 11 can illustrate the correspondingly labeled region of FIG. 6 at the distal region of the flex circuit 314. In some aspects, the flex circuits 314 shown in FIGS. 10 and 11 can be the same flex circuit 314 shown in FIG. 6. In FIG. 10, the conductive traces 316 are formed on the flex circuit 314 in a zig-zag formation at a region 311, and in a linear configuration at a region 312. The conductive traces 316 can continue to other regions of the flex circuit 314, such as the controller region 308, to communicatively couple the transducers 312 to the control circuits 306. In FIG. 11, the conductive traces 316 are formed in an angled configuration in the region 311 and a linear configuration in the region 312. As described above with respect to FIGS. 7-9, the zig-zag and/or angled configurations of the conductive traces 316 can increase the durability and longevity of the conductive traces 316 during use of the imaging device. As the flex circuit 314 of the imaging device bends, flexes, and strains while passing through the tortuous vasculature of the patient, the zig-zag and/or angled configurations of the conductive traces 316 may mitigate risk of fracture and/or kinking of the conductive traces 316 to maintain communication of the transducers 312 with the control circuits 306. While FIGS. 10 and 11 illustrate the distal portion of the flex circuit 314, the disclosure can similarly apply to other portions of the flex circuit 314, such as the conductive traces leading to or extending from the controllers 306.

Figure 12:
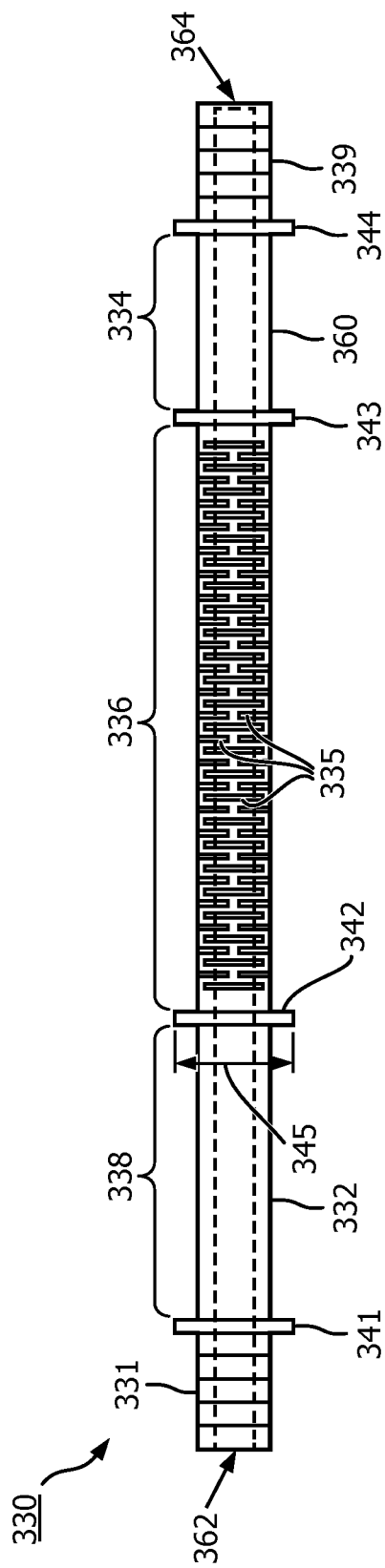
FIG. 12 is a diagrammatic side view of a support member, according to aspects of the present disclosure.

FIG. 12 illustrates a side view of the support member 330. The support member 330 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 330 has a controller portion 338, a transducer portion 334, and a flex joint portion 336 extending between the controller and transducer portions 338, 334. The support member 330 may be variously sized and shaped in different embodiment. For example, while the illustrated embodiment shows a substantially cylindrical support member 330, the support member 330 may comprise other shapes, such as a rectangular prism, ellipsoid, and/or other suitable shape. The support member 330 may be sized and shaped to allow greater flexibility of the intravascular device. For example, the support member 330 may compliment the size and shape the flex circuit 314.

The controller and transducer portions 338, 334 can have an outer profile that is substantially cylindrically-shaped. The flex joint portion 336 can be a bridge extending between the controller and transducer portions 338, 334. In the illustrated embodiment, the flex joint portion 336 can be shaped in a cylindrical manner and extend in a linear manner between the controller and transducer portions 338, 334. For example, outer surfaces of the controller portion 338, the flex joint portion 336, and the transducer portion 334 may form a continuous surface. In other embodiments, the flex joint portion 336 may extend between the controller and transducer portions 338, 334 such that outer surface of the support member 330 is discontinuous. Other configurations of the flex joint portion 336 are also contemplated.

One or more dimensions of the various portions of the support member 330 can correspond to one or more corresponding dimensions of the regions of the flex circuit 314. In some instances, a circumference, width, and/or length of the various portions of the support member 330 can be based on cut, unrolled, and/or flattened state of the flex circuit 314. Corresponding dimensions between the support member 330 and the flex circuit 314 advantageously facilitates support of the various regions 304, 308, 310 of the flex circuit 314.

The controller and transducer portions 338, 334 of the support member 330 can be variously sized and shaped to support the flex circuit when the flex circuit is positioned around the support member. The dimensions of the support member 330 can be selected such that the intravascular device 102 has a diameter between approximately 2 Fr and approximately 10 Fr, for example. In some embodiments, the controller and transducer portions 338, 334 of the support member 330 are similarly sized and shaped. In other embodiments, the controller portion 338 can be larger or smaller than the transducer portion 334. In some embodiments, a length of the controller portion 338 can be between approximately 3 mm and 7 mm, a length of the transducer portion 334 can be between approximately 0.5 mm to 2 mm, and a length of the flex joint portion can be between approximately 2 mm and 10 mm.

The controller, transducer, and flex joint portions 338, 334, 336 can be integrally formed. In some embodiments, the support member 330 can be shaped by removing material from a cylindrical blank. For example, the blank can be machined using a tool to cut, or remove material at cuts 335. Forming the cuts 335 advantageously increases flexibility of the support member 330 by reducing the amount of material contributing to the stiffness of the support member 330. In the illustrated embodiment, the cuts 335 can be removed from the flex joint portion 336. The cuts 335 can extend radially inwards from an outer surface of the support member 330. A lumen 360 can extend longitudinally through the support member 330. The lumen 360 can include a proximal opening 362 at a proximal end of the support member 330, and a distal opening 364 at a distal end of the support member 330. The lumen 360 can be sized and shaped to allow a guide wire to pass therethrough.

The cuts 335 are shown in an alternating pattern. For example, the cuts 335 can be formed by cutting into the support member towards the lumen 360 from a top and bottom side of the support member 330 at a first plurality of points along the support member 330, and cutting radially inward into the support member 330 towards the lumen 360 from a front and back side of the support member 330 at a second plurality of points along the support member 330, wherein the first and second plurality of points are arranged in an alternating fashion. In some embodiments, the support member 330 is molded, such as with an injection molding process. In such instances, the support member 330 including the controller, transducer, and flex joint portions 338, 334, 336, are formed without removing the material indicated by cuts 335. The controller, transducer, and flex joint portions 338, 334, 336 can be integrally formed.

The support member 330 of FIG. 12 comprises a plurality of flanges 341, 342, 343, 344. The flanges 341, 342, 343, 344 may comprise washers or raised portions of the support member 330 at various points along the support member 330. In some embodiments, the flanges 341, 342, 343, 344 can be formed by securing a washer or flange to the cylindrical body 332 of the support member 330. In other embodiments, the flanges 341, 342, 343, 344 can be integrally formed with the other portions of the support member 330 by, for example, removing material from a cylindrical blank. A flange 341 is shown positioned at a proximal portion of the support member 330, near a proximal end of the controller portion 338, while a flange 342 is disposed near a distal end of the controller portion 338. In some aspects, the flanges 341, 342 can define the controller portion 338. The position of the flange 342 may also be described as the proximal end of the flex joint portion 336. A flange 343 is positioned near a distal end of the flex joint portion 336. In some aspects, the flanges 342, 343 can define the flex joint portion 336. The position of the flange 343 may also be described as the proximal end of the transducer portion 334. A flange 344 is positioned near a distal end of the transducer portion 334. In some aspects, the flange 343 and the flange 344 can define the transducer portion 334. The flanges 341, 342, 343, 344 are configured to support a flex circuit, such as the flex circuit 314 of FIG. 6, in a rolled or wrapped configuration. In some embodiments, the flanges 341, 342, 343, 344 can support the flex circuit 314 away from the cylindrical body 332 of the support member 330. The flanges 341, 342, 343, 344 can each have a diameter, such as diameter 349. In some embodiments, the flanges 341, 342, 343, 344 have the same diameter 349. In other embodiments, one or more of the flanges 341, 342, 343, 344 can have different diameters. The diameter of the flanges 341, 342, 343, 344 can be larger than a diameter of the body 332 of the support member 330.

One or more of the flanges 341, 342, 343, 344 can be electrically conductive to facilitate grounding. Each of the flanges 341, 342, 343, 344 can be placed to define the portions of the support member 330 to provide support and various components of the flex circuit 314. For example, the flanges 341, 342, which can define the controller portion 338, can provide support to the controller region 308 of the flex circuit 314 to protect and/or provide structure support to the control circuits 306. Similarly, the flanges 343, 344 can define the transducer portion 334 and can protect and/or provide structural support to the transducer region 304 of the flex circuit 314 to facilitate proper operation of the plurality of transducers 312. The flanges 341, 342, 343, 344 can also provide a space between the flex circuit and the cylindrical body 332 of the support member 330 to provide room for the components of the flex circuit 314. As described below, the flex circuit 314 may be wrapped or rolled around the support member 330 such that one or more components of the flex circuit 314 project radially inward toward the cylindrical body 332 of the support member 330, such that a smooth side of the flex circuit 314 is positioned on the outside of the intravascular device 300.

Figure 13:
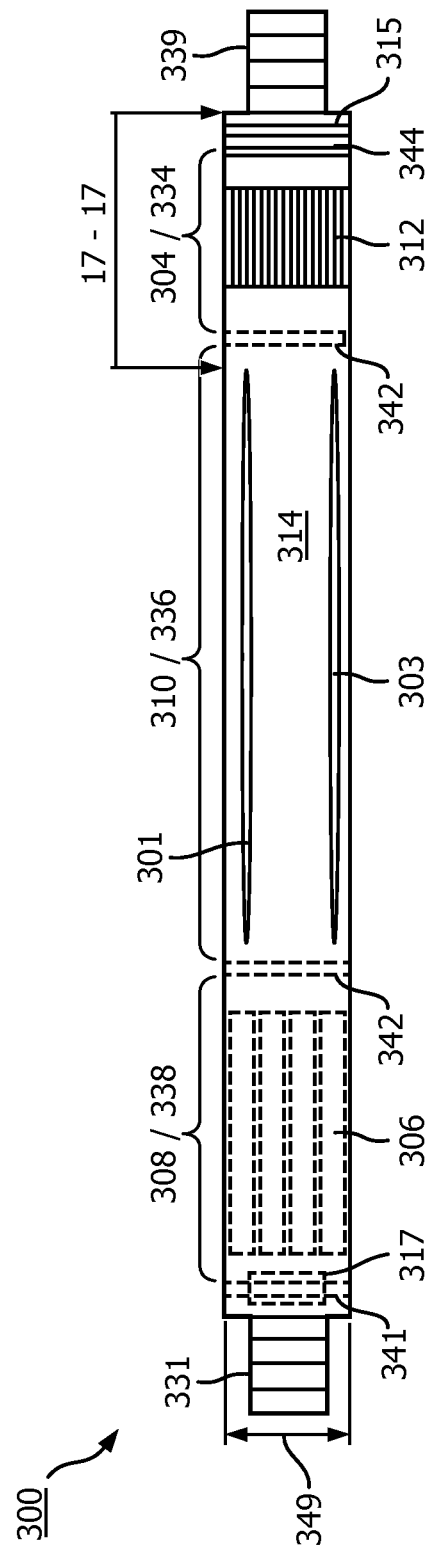
FIG. 13 is a diagrammatic side view of a support member and a flex circuit in a rolled configuration, according to aspects of the present disclosure.

FIG. 13 is a diagrammatic side view of a distal portion of an ultrasonic imaging device 300. For example, an imaging assembly, such as the flex circuit 314 positioned around the support member 330, can be disposed at the distal portion of a flexible elongate member (e.g., a catheter). The controller, transducer, and flex joint portions 338, 334, 336 of the support member 330 support the flex circuit 314 while advantageously minimizing the amount of material of the support member 330, and increasing flexibility and maneuverability of the imaging device 300. The transducer region 304 and the controller region 308 can have a cylindrical or cylindrical toroid configuration when rolled around the support member 330. The lumen 360, sized and shaped to receive a guide wire, extends longitudinally through the support member 330. The transducer region 304 of the flex circuit 314 is positioned around transducer portion 334 of the support member 330 such that the transducers 312 are adjacent to the transducer portion 334. The controller region 308 of the flex circuit 314 is positioned around the controller portion 338 of the support member 330, such that the control circuits 306 are adjacent to the controller portion 338. The dimensions of the device 300 can be selected such that the device 300 has a diameter 349 between approximately 2 Fr and approximately 10 Fr, for example. In some embodiments, the diameter 349 of the device 300 may be substantially the same as the diameter 345 of one or more of the flanges 341, 342, 343, 344.

The transition region 310 of the flex circuit 314 is aligned with the flex joint portion 336 of the support member 330. The support member 330 can be shaped such that that flex joint portion 336 supports the transition region 310. In that regard, the transition region 310 can be adjacent to the flex joint portion 336 while the flex circuit 314 is positioned around the support member 330. The flex circuit 314 can be supported by the plurality of flanges 341, 342, 343, 344 with the components of the flex circuit projecting inward toward the cylindrical body 332, such that the outer surface of the imaging device 300 comprises a smooth surface.

In other embodiments, the transition region 310 of the flex circuit 314 extends between the controller and transducer regions 308, 304 in a linear, curved, spiral, and/or other suitable manner. Spiral wrapping of at least a portion of the flex circuit 314 is described in U.S. Provisional App. No. 62/315,395, titled "Single Unibody Designs", and filed Mar. 30, 2016, the entirety of which is hereby incorporated by reference herein. The dimensions of the flex circuit 314 and/or the support member 330 may vary in different embodiments. For example, the proximal and/or distal portions may be sized to respectively accommodate control circuits 306 and transducers 312. As described below with respect to FIG. 17, in some instances, the flex circuit 314 may be radially spaced from the support member 330, and an acoustic dampening material, or acoustic backing material 346, can be disposed between in a space between the flex circuit 314 and the support member 330 to facilitate operation of the transducers.

The flexible substrate 314 can be configured to hermetically seal one or more of the components of the substrate 314 (e.g., transducers 312, control circuits 306) in some embodiments. For example, the flexible substrate may be rolled or wrapped around the flanges 341, 342, 343, 344, so as to create hermetically sealed spaces between the substrate 314 and the support member 330. In some embodiments, the imaging device 300 may further comprise a flexible tubing configured to surround the flex circuit 314 once the flex circuit 314 has been rolled onto the support member 330. The flexible tubing may comprise a shrinkable tubing, in some instances. The shrinkable tubing may shrink in response to heat. The flexible tubing may comprise a low durometer, or soft, material. The flexible tubing may be configured to seal and/or protect one or more components of the flex circuit 314, such as the transducers 312 and/or the control circuits 306.

Generally, the imaging device 300 can be a catheter, a guide catheter, or a guide wire. The imaging device 300 includes a flexible elongate member, or elongate body (e.g., outer member 254 and/or inner member 256). The imaging assembly (e.g., flex circuit 314 and/or support member 330) can be disposed at the distal portion of the flexible elongate member. As used herein, "elongate member" or "flexible elongate member" includes at least any thin, long, flexible structure structurally arranged (e.g., sized and/or shaped) to be positioned within a lumen of the anatomy. For example, a distal portion of the flexible elongate member is positioned within a lumen, while a proximal portion of the flexible elongate member is positioned outside of the body of the patient. The flexible elongate member can include a longitudinal axis. In some instances, the longitudinal axis can be a central longitudinal axis of the flexible elongate member. In some embodiments, the flexible elongate member can include one or more polymer/plastic layers formed of various grades of nylon, Pebax, polymer composites, polyimides, and/or Teflon. In some embodiments, the flexible elongate member can comprise stainless steel. In some embodiments, the flexible elongate member can include one or more layers of braided metallic and/or polymer strands. The braided layer(s) can be tightly or loosely braided in any suitable configuration, including any suitable per in count (pic). In some embodiments, the flexible elongate member can include one or more metallic and/or polymer coils. All or a portion of the flexible elongate member may have any suitable geometric cross-sectional profile (e.g., circular, oval, rectangular, square, elliptical, etc.) or non-geometric cross-sectional profile. For example, the flexible elongate member can have a generally cylindrical profile with a circular cross-sectional profile that defines an outer diameter of the flexible elongate member. For example, the outer diameter of the flexible elongate member can be any suitable value for positioning within the anatomy, including between approximately 1 Fr and approximately 15 Fr, including values such as 3.5 Fr, 5 Fr, 7 Fr, 8.2 Fr, 9 Fr, and/or other suitable values both larger and smaller. Diameters 345 and 349 can have similar values in some instances.

FIG. 14 illustrates a diagrammatic side view of a support member 430, according to some embodiments of the present disclosure. The support member 430 can be similar to the support members described herein, including the support members 230 and 330, in some aspects. The support member 430 includes a flex joint portion 436 positioned between controller and transducer portions 438, 434. Similar to the flex joint portion 336 shown in FIG. 12, the flex joint portion 436 of FIG. 14 advantageously enables the support member 430 to bend at the flex joint portion 436, which may increase maneuverability of the intravascular device within vasculature. The support member 430 of FIG. 14 may comprise fewer flanges 443, 444 than the support member 330 shown in FIG. 12. The support member 430 can comprise a flange 443 and a flange 444 at or near a transducer portion 434 of the support member 430, and a grounding area 441 at or near a controller portion 438 of the support member 430. The 443, 444 can be configured to provide structural support to a corresponding transducer region of a flex circuit, such as the transducer region 304 of the flex circuit 314 of FIG. 6. The support member 430 can also comprise a plurality of cuts 435 configured to increase flexibility of the support member 430 in the flex joint portion 436.

The grounding area 441 may be described as a "solder bump" in some embodiments. The grounding area 441 may be configured to electrically couple to a corresponding grounding region of a flex circuit to facilitate grounding of the flex circuit via the support member 430. The grounding area 441 of the support member 430 can comprise an area of raised material, such as a metal, configured to facilitate a secure electrical contact with a corresponding grounding region of a flex circuit. In some embodiments, the grounding area 441 can comprise a solder agent used during assembly of an intravascular device to create a solder connection of the grounding area 441 with a corresponding grounding region of a flex circuit in response to heat. In the illustrated embodiment, the transducer portion 334 includes flanges 443, 444 configured to support a corresponding transducer region of a flex circuit, such as the transducer region 304 of the flex circuit 314. The flanges 443, 444 are configured to support the transducers 312 and transducer region 304 away from the support member 430 (e.g., radially spaced), such that a space is provided wherein an acoustic backing material can be included to improve performance of the transducers 312. In contrast to the transducer region 304, the controller region 308 may not require and/or benefit from a space between the controllers 306 and the support member 430. Thus, the support member 430 does not include flanges at the controller portion 438. The controllers 306 and/or controller region 308 of the flex circuit 314 can surround and abut the support member 430 at or near the controller portion 438.

FIG. 15 is a diagrammatic side view of a support member 530 to be used in an intravascular imaging device. The support member 530 can be similar to the support members described herein, including the support members 230, 330, and 430, in some aspects. The support member 530 can be formed of different materials having differing degrees of flexibility. The support member 530 can also be formed of separate components that are fixedly joined. For example, the support member 530 can include a controller portion 538, a transducer portion 534, and a flex joint portion 536.

The flex joint portion 536 of the support member 530 can include a coil 535 or spring disposed between and coupled to the controller portion 538 and the transducer portion 534. The coil 535 can be fixedly coupled to the other portions of the support member 530 in any suitable manner, including a solder and/or adhesives. In some embodiments, the coil 535 may be formed with the other portions of the support member 530 from a solid body, or unibody (e.g., a cylindrical blank), by machining and/or removing material from the flex joint portion 536 to create the coil 535 or spring. The coil 535 may behave similarly to the cuts 335, 435 of the support members of FIGS. 12 and 14 to provide increased flexibility and maneuverability to an imaging device.

The support member of FIG. 14 includes a plurality of flanges 541, 542, 543, 544 configured to support a flex circuit. The flanges 541, 542, 543, 544 of the support member 530 may be configured in a similar manner as the flanges of the embodiment of FIGS. 12 and 13. Each of the controller portion 538, the flex joint portion 536, and the transducer portion 534 may comprise a length corresponding to a length of a controller region, a transition region, and a transducer region of a flex circuit, respectively. The corresponding lengths of the portions of the support member may be greater than, less than, or substantially equal to the corresponding lengths of the portions of the support members 330. 430 shown in FIGS. 12 and 14. In some embodiments, the length of one portion of the support member of FIG. 14 may be greater than the length a corresponding portion of the support member 330 of FIG. 12, while a length of another portion of the support member 430 of FIG. 14 is less than a length of the corresponding portion of the support member 330 of FIG. 12, and vice versa.

FIG. 16 is a diagrammatic side view of an intravascular imaging device 600, including a support member 630 and a flex circuit 614, according to some embodiments of the present disclosure. The support member 630 of FIG. 16 can comprise an elongate body 632 formed of a polymer. The polymer may be malleable or soft such that it can be deformed to receive one or more components of the flex circuit 614. For example, as the flex circuit 614, including a plurality of transducers 612 and a plurality of control circuits 606, is wrapped around the malleable polymer elongate body 332, the polymer may deform such that the control circuits 606 and transducers 612 are partially embedded into the polymer elongate body 632, and such that the flex circuit 614 lies substantially flat and/or flush against an outer surface of the elongate body 632. In some embodiments, the support member 630 can include a conductive agent in the polymer to facilitate grounding of the flex circuit 614. In some embodiments, the polymer elongate body 632 can comprise an acoustic dampening agent configured to improve performance of the transducers 612. For example, the acoustic dampening agent can impede the propagation of ultrasonic energy emitted by the transducers 612 inward (e.g., towards the support member 630), such that the ultrasonic energy is directed outward (e.g., towards the anatomy in which the intraluminal imaging device 600 is positioned). As the malleable polymer of the support member 630 can be conductive to facilitate grounding, and can deform to create a substantially flush or smooth outer surface of the imaging device, the support member 630 does not include supporting flanges such as those described in FIGS. 12-15.

The support member 630 can include grounding portions 641, 644 configured to facilitate grounding between the grounding regions of the flex circuit (e.g., 315, 317), and the support member 630. In some embodiments, the grounding portions 641, 644 can comprise soldering pads wherein the corresponding grounding regions of the flex circuit can be soldered.

In some embodiments, the malleable polymer may be configured to harden, or set, in response to heat. A baking process may harden the support member to secure the flex circuit 614 to the elongate body 632. Once hardened, the support member 630 may still be flexible in one or more aspects to navigate through tortuous regions of the vasculature of a patient. Thus, although the baking or hardening process may set or harden the support member 630 in some aspects, the support member 630 may still be capable of bending or flexing at one or more areas of the support member 630.

Figure 17:
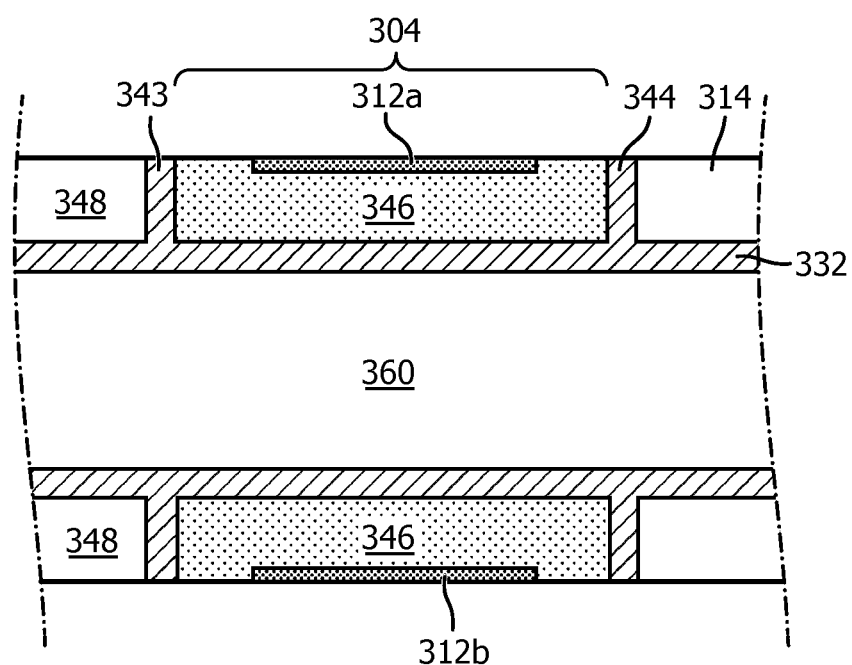
FIG. 17 is a diagrammatic cross-sectional view of a distal portion of a support member and a flex circuit in a rolled configuration, according to some aspects of the present disclosure.

FIG. 17 is a diagrammatic cross-sectional view of the transducer region of the imaging device of FIG. 13 taken along line 17-17. The support member 330 is wrapped with the flex circuit 314 such that the transducer region 304 comprising the plurality of transducers 312 is at least partially disposed within a space between the flange 343 and the flange 344. The space formed between the flange 343 and the flange 344 of the support member 330 and the flex circuit 314 can be filled with an acoustic backing material 346. The acoustic backing material 346 can be a liquid in some instances. Other spaces formed between the flex circuit 314 and the support member 330, such as the space 348 between the flange 343 and the flange 342, may not comprise an acoustic backing material. The grounding region at the distal portion of the flex circuit 314 can be in contact with the flange 344 to facilitate electrical grounding of the flex circuit 314. The lumen 360 can be partially defined by the elongate body 332 of the support member 330, and can be configured to receive a guide wire.

Figure 18:
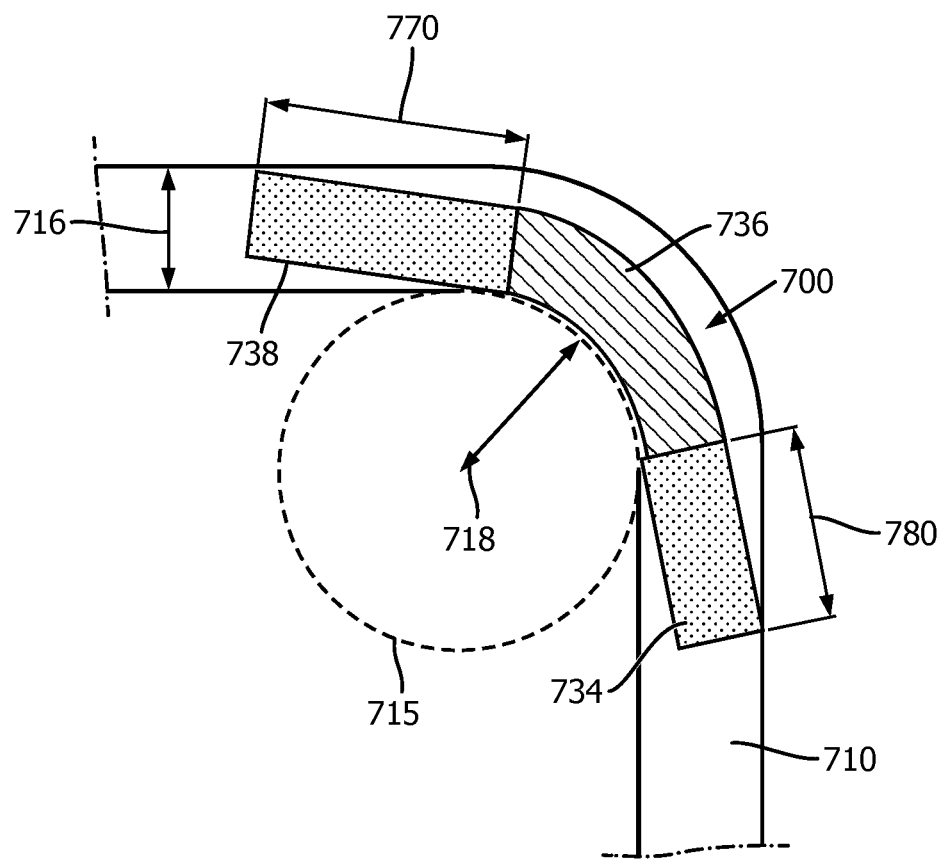
FIG. 18 is a diagrammatic top view of an intravascular imaging device in a tortuous portion of a blood vessel, according to aspects of the present disclosure.

FIG. 18 is a diagrammatic side view of a distal portion of an intravascular imaging device 700 shown traversing a tortuous region of a blood vessel 710. FIG. 17 may illustrate similar aspects as those depicted in FIG. 5. The intravascular imaging device 700 may comprise a support member and flex circuit as illustrated in FIGS. 12 and 13, wherein the support member comprises a flex joint portion 736 between a controller portion 738 and a transducer portion 734. The controller portion 738 and transducer portion 734 can be relatively more rigid than the flex joint portion 736. The controller portion may be characterized by a stiff length 770, and the transducer portion may be characterized by a stiff length 780. Each of the stiff lengths 770, 780 may be less than the stiff length 170 of the device 102 shown in FIG. 5. The flex joint portion 736 may be configured to bend or flex to navigate tortuous regions of the vasculature, such as the bend of the blood vessel 710. Having the controller portion 738 and transducer portion 734 separated by the flex joint portion 736 may enable the intravascular imaging device 700 to navigate more tortuous regions of the vasculature than the embodiment illustrated in FIG. 5. For example, the blood vessel 710 shown in FIG. 17 may comprise an inside diameter 716 which is smaller than the inside diameter 16 of the blood vessel 10 of FIG. 5. Furthermore, the blood vessel 710 of FIG. 17 may have a sharper bend than the bend of the blood vessel 10 illustrated in FIG. 5. For example, the bend of the blood vessel 710 of FIG. 17 may be partially characterized by a circle 715 having a radius 718, which is less than the radius 18 of the circle 15 of FIG. 5. In other words, the device 102 of FIG. 5 may be unable to safely traverse the region of the blood vessel 710 illustrated in FIG. 17. By contrast, the device 700 of FIG. 17 may be capable of safely traversing the region of the blood vessel 710, which may be due, in part, to the implementation of the flex joint portion 736 between the controller portion 738 and transducer portion 734.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging device, comprising:
   a flexible substrate comprising:
      a plurality of ultrasound transducer elements configured to obtain imaging data, wherein the plurality of ultrasound transducer elements is are disposed on a first segment of the flexible substrate;
      a plurality of control circuits in communication with the plurality of ultrasound transducer elements, wherein the plurality of control circuits are disposed on a second segment of the flexible substrate;
      a plurality of conductive traces extending between the plurality of ultrasound transducer elements and the plurality of control circuits;
      a first grounding region disposed on the first segment located distal to the plurality of ultrasound transducer elements, wherein the first grounding region is configured to facilitate grounding of the plurality of ultrasound transducer elements; and
      a second grounding region disposed on the second segment proximate to the plurality of control circuits such that the second grounding region is distinct from the first grounding region, wherein the second grounding region is configured to facilitate grounding of the plurality of control circuits;
   a catheter configured to be positioned within a body lumen of a patient; and
   a support member coupled to a distal portion of the catheter and defining guidewire lumen, wherein the flexible substrate is wrapped around the support member, the support member comprising:
      a body; and
      a plurality of flanges comprising a diameter larger than the body such that the flexible substrate is radially spaced from the body,
   wherein the plurality of flanges comprises:
      a first flange and a second flange configured to support the first segment of the flexible substrate such that the first flange and the second flange define a transducer portion of the body aligned with the plurality of ultrasound transducer elements; and
      a third flange and a fourth flange configured to support the second segment of the flexible substrate such that the third flange and the fourth flange define a control portion of the body aligned with the plurality of control circuits.

2. The device of claim 1, wherein the support member is generally cylindrical.

3. The device of claim 1, wherein the support member comprises stainless steel.

4. The device of claim 1, wherein the plurality of ultrasound transducer elements comprises an ultrasonic transducer array positioned around the transducer portion of the body.

5. The device of claim 1, further comprising a shrink tubing positioned around and configured to hermetically seal at least one of:
   the plurality of ultrasound transducer elements;
   the plurality of control circuits; or
   the plurality of conductive traces.

6. The device of claim 1,
   wherein the first flange is positioned at a proximal portion of the transducer portion and the second flange is positioned at a distal portion of the transducer portion, and
   wherein the third flange is positioned at a proximal portion of the control portion and the fourth flange is positioned at a distal portion of the control portion.

7. The device of claim 1,
   wherein at least one of the first grounding region or the second grounding region of the flexible substrate is electrically coupled to a grounding area of the support member to facilitate grounding of the flexible substrate,
   wherein the at least one of the first grounding region or second grounding region of the flexible substrate is longitudinally aligned and contacts the grounding area of the support member.

8. The intraluminal ultrasound imaging device of claim 1, wherein the flexible substrate comprises an interface region comprising at least one of a capacitor or a testing region.

9. The intraluminal ultrasound imaging device of claim 1, wherein the body extends proximal of the plurality of flanges and distal of the plurality of flanges such that the second flange is spaced from a distal end of the support member and the third flange is spaced from a proximal end of the support member.

10. The intraluminal ultrasound imaging device of claim 1,
    wherein the second flange is electrically conductive, and
    wherein the second flange is aligned with and contacts the first grounding region.

11. The intraluminal ultrasound imaging device of claim 1, wherein the second grounding region is located proximal to the plurality of control circuits such that the first grounding region and the second grounding region are spaced from the plurality of conductive traces extending between the plurality of ultrasound transducer elements and the plurality of control circuits.

12. The intraluminal ultrasound imaging device of claim 1, wherein the plurality of ultrasound transducer elements and the first grounding region are disposed on a first side of the flexible substrate.

13. The device of claim 1, wherein the support member comprises a polymer and a conductive agent.

14. The device of claim 13, wherein the polymer comprises an acoustic dampening material.

15. The device of claim 1, further comprising acoustic backing material disposed between the body and the plurality of ultrasound transducer elements.

16. The device of claim 15, wherein the flexible substrate comprises one or more slot openings configured to facilitate flexing of the flexible substrate.

17. The intraluminal ultrasound imaging device of claim 1, wherein the body comprises a flex joint portion disposed between the first flange and the fourth flange, wherein the flex joint portion is aligned with the plurality of conductive traces, and wherein the flex joint portion is more flexible than the transducer portion and the control portion.

18. The device of claim 17, wherein the flex joint portion forms a central segment of the support member.

19. The intraluminal ultrasound imaging device of claim 17, wherein the support member comprises: a top side, a bottom side, a front side, and a back side, wherein the flex joint portion comprises a flexible element, wherein the flexible element alternates between:
   a plurality of first cuts extending radially inward from the top side and the bottom side towards the guidewire lumen; and
   a plurality of second cuts extending radially inward from the front side and the back side towards the guidewire lumen, wherein the plurality of first cuts and the plurality of second cuts are non-continuous with one another.

20. An intraluminal ultrasound imaging system, comprising:
   an intraluminal imaging device, comprising:
      a catheter configured to be positioned within a body lumen of a patient; and
      an imaging assembly disposed at a distal portion of the catheter and configured to obtain imaging data associated with the body lumen, the imaging assembly comprising:
         a support member around which a plurality of transducer elements are positioned;
         a plurality of control circuits;
         a first grounding region located distal to the plurality of transducer elements;
         a second grounding region disposed proximate to the plurality of control circuits; and
         a plurality of communication lines extending between the plurality of transducer elements and the plurality of control circuits,
      wherein the first grounding region is configured to facilitate grounding of the plurality of transducer elements,
      wherein the second grounding region is distinct from the first grounding region and is configured to facilitate grounding of the plurality of control circuits, and
      wherein the support member defines a guidewire lumen, wherein the support member comprises:
         a body; and
         a plurality of flanges comprising a diameter larger than the body,
         wherein the plurality of flanges comprises:
            a first flange and a second flange defining a transducer portion of the body aligned with the plurality of transducer elements; and
            a third flange and a fourth flange defining a control portion aligned with the plurality of control circuits; and
   a computing device in communication with the intraluminal imaging device and configured to output, to a display, an image of the body lumen based on the obtained imaging data.

21. The system of claim 20, wherein the intraluminal imaging device comprises an intravascular ultrasound (IVUS) device.

* * * * *